(12) United States Patent
Oon et al.

(10) Patent No.: US 7,037,682 B2
(45) Date of Patent: May 2, 2006

(54) IN VITRO ACTIVITY ASSAY FOR HUMAN HEPATITIS B VIRUS (HBV) DNA POLYMERASE, AND ITS USE FOR SCREENING FOR INHIBITORS OF HBV DNA POLYMERASE

(75) Inventors: Chong Jin Oon, Singapore (SG); Wei Ning Chen, Singapore (SG); Gek Keow Lim, Singapore (SG); Ai Lin Leong, Singapore (SG)

(73) Assignee: Government of the Republic of Singapore, Singapore (SG)

( * ) Notice: Subject to any disclaimer, the term of this patent is extended or adjusted under 35 U.S.C. 154(b) by 247 days.

(21) Appl. No.: 10/231,405

(22) Filed: Aug. 28, 2002

(65) Prior Publication Data

US 2003/0082529 A1    May 1, 2003

Related U.S. Application Data

(62) Division of application No. 09/674,465, filed on Jun. 18, 2001, now Pat. No. 6,593,082.

(30) Foreign Application Priority Data

Mar. 13, 1999    (WO) ..................... PCT/SG99/00017

(51) Int. Cl.
*C12P 21/06*    (2006.01)
*C12P 19/34*    (2006.01)
*C07H 21/04*    (2006.01)

(52) U.S. Cl. .................. 435/69.1; 435/69.1; 435/91.2; 536/24.33

(58) Field of Classification Search .................. 435/6, 435/15, 194, 69.1, 69.3, 5
See application file for complete search history.

(56) References Cited

U.S. PATENT DOCUMENTS 5,492,817 A    2/1996    Thompson et al. ........ 435/68.1

FOREIGN PATENT DOCUMENTS

WO    WO89/06700    7/1989
WO    WO 94/05809    3/1994

(Continued)

OTHER PUBLICATIONS

Chayama, et. al., Emergence and Takeover of YMDD Motif Mutant Hepatitis B Virus During Long-Term Lamivudine Therapy and Re-Takover by Wild Type After Cessation of Therapy, Jun. 1998, Hepatology, vol. 27, No. 6, 1711-1716.*

(Continued)

*Primary Examiner*—James Housel
*Assistant Examiner*—M. Franco Salvoza
(74) *Attorney, Agent, or Firm*—Shirley Chen; Wilson Sonsini Goodrich & Rosati (57) ABSTRACT

The present invention provides an in vitro activity assay for human hepatitis B virus (HBV) DNA polymerase, which comprises using, as the 5' oligonucleotide in PCR amplification of HBV DNA polymerase from a sample, an oligonucleotide into which has been incorporated the SP6 viral polymerase promoter, directly transcribing and translating the PCR products in the presence of a radio-labelled agent and measuring the priming of the HBV DNA polymerase. The present invention also provides the use of such an assay to assay activity of various serum samples, to screen for inhibitors of the HBV DNA polymerase and to test and/or screen potential anti-HBV drugs for their ability to inhibit DNA priming activity of human HBV DNA polymerase.

10 Claims, 4 Drawing Sheets

FOREIGN PATENT DOCUMENTS

| | | |
|---|---|---|
| WO | WO 94/05812 | 3/1994 |
| WO | WO 95/17523 | 6/1995 |
| WO | WO 96/10649 | 4/1996 |

OTHER PUBLICATIONS

Wang and Seeger, The Reverse Transcriptase of Hepatitis B Virus Acts as a Protein Primer for Viral DNA Synthesis, Cell, Nov. 1992, vol. 71, 663-670.*

Li et al. Expression of an enzymatically active polymerase of human hepatitis B virus in a coupled transcription-translation system (1999) Biochemistry and Cell Biology, 77:2 pp. 119-126.*

Martemyanov, K.A., et al., "Direct Expression of PCR Products in a Cell-Free Transcription/Translation System: Synthesis of Antibacterial Peptide Cecropin," *FEBS Letters 414* (1997) pp. 268-270.

Sprengel, Isolation and Characterization of a Hepatitis B Virus Endemic in Herons, Journal of Virology, vol. 62, No. 10, p. 3832-3839, Oct. 1988.

Howe, A., et al., *Biochemical and Biophysical Research Communications,* "Duck hepatitis B virus polymerase produced by in vitro transcription and translation possesses DNA and reverse transcriptase activities", vol. 189, No. 2, pp. 1170-1176, Dec. 15, 1992.

* cited by examiner

Fig. 6 Anti-priming Effects of Nucleotide Analogs

IN VITRO ACTIVITY ASSAY FOR HUMAN HEPATITIS B VIRUS (HBV) DNA POLYMERASE, AND ITS USE FOR SCREENING FOR INHIBITORS OF HBV DNA POLYMERASE

CROSS REFERENCE TO RELATED APPLICATIONS

This application is a divisional of U.S. application Ser. No. 09/674,465, filed on Jun. 18, 2001, now U.S. Pat. No. 6,593,082, which claims priority to PCT Application No. PCT/SG99/00077, filed Mar. 13, 1999. These applications are incorporated herein by reference in their entirety.

BACKGROUND OF THE INVENTION

Polymerases are enzymes of fundamental importance to living organisms. They are responsible for the synthesis of nucleic acids and their transformation into other nucleic acids necessary for the synthesis of proteins. Polymerases are, therefore, found in all types of cells including the causative DNA virus for hepatitis B virus (HBV).

HBV is a cause of hepatitis, one of the most common infectious human diseases, and the resulting hepatocellular carcinoma (HCC) is one of the most common cancers worldwide. The most effective way in preventing HBV infection and disease to date is through immunization against HBV. The currently licensed HBV vaccines consist of the major surface antigen (HBsAg) in either its natural form (plasma-derived) or recombinant form (purified from yeast cells). The vaccine-induced antibodies have been shown to bind to the most antigenic 'a' epitope located within residues 124 to 147 of HBsAg, resulting in effective neutralization of HBV replication.

Although such active vaccination programme has resulted in a decrease of HBV infection in the population, an increasing number of mutations located within the 'a' epitope have been emerging. These vaccine-induced HBV mutants are of concern, as they are capable of escaping the currently available immuno-based diagnostic system and able to replicate independently.

The fact that mutations on the 'a' epitope of HBsAg give rise to amino acid substitutions in the overlapping HBV DNA polymerase, particularly by their location within the reverse transcriptase domain, may imply that these vaccine-induced mutants have altered reverse transcriptase activity, a key factor for the viral replication.

HBVs are DNA viruses that replicate their genomes by reverse transcription of an RNA intermediate. Packaging of this RNA pregenome into nucleocapsides and initiation of the replication depends primarily on the interaction of the HBV DNA polymerase with the encapsidation signal. There are two copies of the encapsidation signals on the pregenomic RNA. Only the 5' copy functions as a template for the priming reaction. Following initiation of the minus-strand DNA synthesis, the DNA oligomer (4 nucleotides) is transferred by an unknown mechanism to the 3' end of pregenomic RNA, where it hybridizes to its complementary sequences. Reverse transcription then continues toward the 5' end of the RNA template. The interaction between the HBV DNA polymerase and the pregenomic RNA occurs as a covalent link between the N-terminally located tyrosine residue on the DNA polymerase and a specific nucleotide within the encapsidation signal. The HBV reverse transcriptase is one of the four domains within the large DNA polymerase. Other domains include: i) the N-terminal protein, which is responsible for the covalent association of the polymerase to the pregenomic RNA; ii) the spacer region which is tolerant for mutations; and iii) the RNAse H domain involved in the degradation of the mRNA intermediate.

Similarly to other polymerases, detection of the HBV DNA polymerase activity in vitro can be used in the following three situations:

Characterization of a newly isolated virus as a replicative virus and assess the differences with regard to other known viruses. This is particularly relevant for HBV variants with mutations on their surface antigens;

Determination of isolation success of virus from the test material of a subject known to be infected;

Assessment of in vitro efficiency of inhibitors of polymerases that may be antiviral agents.

Various systems have been established to measure the HBV DNA polymerase activity in intro in the absence of viral replication and other viral proteins. One interesting finding has been the fact that a detectable priming activity of HBV DNA polymerase requires not only the N-terminal protein but also a functional reverse transcriptase domain. One common feature of these systems is therefore the detection of the priming activity of HBV DNA polymerase, indicative of HBV DNA polymerase activity. Two of such systems utilize the duck HBV (DHBV) DNA polymerase, and both have demonstrated reverse transcriptase activity that is template dependent and protein primed. One of the DHBV systems utilizes in vitro translation of DHBV DNA polymerase to obtain lysates that contain a functional DNA polymerase, while the other system packages an active fusion protein of DHBV DNA polymerase in a virus-like particle from the yeast retrotransposon Ty1. Active DNA polymerase has been measured by its priming activity, as indicated by the radio-labeled protein in the presence of priming nucleotide (i.e. [$\alpha$-$^{32}$P] dGTP for DHBV DNA polymerase). A similar activity assay has recently been reported for the human HBV DNA polymerase. A 350 base pairs 3' non-coding region of the polymerase containing the encapsidation signal has been included in all reported constructs, therefore pointing to its importance for in vitro activity assay.

One direct application of the in vitro activity assay for human HBV DNA polymerase may be the screening of novel antiviral agents. Antiviral therapy of chronic HBV infection still remains a problem since several clinical trials have shown that a sustained response to interferon or nucleoside analogs is observed in only 30 to 40% of the patients studied. This response rate is even lower in long-term HBV carriers and in immunocompromised patients. The design of new protocols for chemotherapy to eliminate HBV is needed since the majority of the patients will not clear the viral infection and, therefore, will be at great risk of developing progressive liver disease and hepatocellular carcinoma (HCC). It will also be of particular interest to assess the antiviral effects of such agents on human HBV surface antigen mutants.

Limiting factors exist, however, for antiviral testing using the established in vitro activity assays for human HBV DNA polymerase. One of these has been the cloning step that places the coding region of the HBV DNA polymerase under the control of a viral polymerase promoter (e.g. SP6 or T7) on a plasmid (i.e. pGEM-T) is required in all established systems. In addition, HBV DNA polymerase expressed in some systems requires further purification (i.e. immunoprecipitation) prior to its activity assay. These tedious manipulations are not practical in view of the large number of HBV mutants.

SUMMARY OF THE INVENTION

According to the first aspect of the present invention, there is provided an in vitro activity assay for human hepatitis B virus (HBV) DNA polymerase, which comprises using, as the 5' oligonucleotide in PCR amplification of HBV DNA polymerase from a sample, an oligonucleotide into which has been incorporated the SP6 viral polymerase promoter, directly transcribing and translating the PCR products in eukaryotic cell-free lysates and measuring the priming of the HBV DNA polymerase in the presence of a radio-labelled agent.

According to a second aspect of the present invention, there is provided the use of an assay according to the first aspect of the invention to assay activity of various serum samples and/or to screen for inhibitors of the HBV DNA polymerase.

According to a third aspect of the present invention, there is provided the use of an assay according to the first aspect of the invention to test and/or screen potential anti-HBV drugs for their ability to inhibit DNA priming activity of human HBV DNA polymerase. Such a use preferably includes the steps of:

a) preparing at least one sample in a defined volume of assay buffer, each sample containing in vitro translated human HBV DNA polymerase protein in eukaryotic cell-free lysate using linear PCR product as template, an RNA template for HBV minus strand synthesis which includes a sequence capable of forming a stem loop structure, b) preparing a control sample in an equivalent volume of the assay buffer, the control sample containing in vitro translated human HBV DNA polymerase protein using linear PCR product as template and an RNA template for HBV minus strand synthesis which includes a sequence capable of forming a stem loop structure, essential for binding and priming of the human HBV DNA polymerase, c) incubating the samples to obtain a complex comprising DNA polymerase and the radio-labelled agent, d) separating the complexes from the assay buffer, and e) measuring the amount of radio-labelled agent in each separated complex, the amount being indicative of the DNA priming activity of the human HBV DNA polymerase.

Step c), d) and e) above may be replaced by:

c) incubating each said test tube and said control tube with equivalent amounts of a radio-labeled nucleotide triphosphate comprising the first nucleotide incorporated into said HBV minus strand DNA, under defined conditions favorable to DNA priming activity of said human HBV DNA polymerase, resulting in the formation of a complex comprising said DNA polymerase and said radio-labeled nucleotide triphosphate;

d) separating said complex from said assay buffer in each said test tube and said control tube by filtration through nitrocellulose membrane;

e) measuring the amount of said radio-labeled nucleotide triphosphate in each said separated complex, said amount being indicative of said DNA priming activity of said human HBV DNA polymerase;

f) comparing the respective amounts of said radio-labeled nucleotide triphosphate in said separated complexes which remained bound to the nitrocellulose membrane of each said test tube and said control tube, a decrease in the amount of said radio-labeled nucleotide triphosphate in said separated complexes of said test tube as compared to said control tube being indicative of inhibition of said DNA priming activity of said human HBV DNA polymerase by said potential anti-HBV drugs.

The present invention concerns a simplified activity assay for the hepatitis B virus (HBV) DNA polymerase, which assay is potentially more rapid than previous assays. The method involves the incorporation of the SP6 viral polymerase promoter into an oligonucleotide, which is then used as the 5' oligonucleotide in PCR amplification of the HBV DNA polymerase from serum samples. The PCR products, containing the entire coding region and a 300 bp 3' non-coding region with the encapsidation signal, are directly transcribed and translated in the wheat germ cell-free extract. The priming of the HBV DNA polymerase to the intermediate RNA template, the key indicator of its enzymatic activity, is measured in the presence of the radio-labeled [$\alpha$-$^{32}$P] dTTP. Applications of the present invention cover the activity assay from various serum samples (including those of HBV with mutations on the major surface antigen), and screening for inhibitors of the HBV DNA polymerase.

The invention provides a simplified process for assaying in vitro the human HBV DNA polymerase activity directly from the linear DNA template amplified from serum samples. The protein involved in the activity assay is generally produced in the wheat germ cell-free system by coupling the transcription and translation from the linear DNA template, which contains a SP6 viral polymerase promoter at its 5' end.

For the achievement of this and other objects, the present invention provides a method for producing the HBV DNA polymerase directly from linear DNA fragment amplified from serum sample. In the presence of the radiolabeled agent, such as [$\alpha$-$^{32}$P] dTTP, the resulting protein is assayed for its priming activity, a crucial step in hepatitis B viral replication.

DETAILED DESCRIPTION OF THE INVENTION

The present invention provides a simple, sensitive and rapid assay that is specific for HBV DNA polymerase activity. The present invention includes a method detecting HBV DNA polymerase activity from serum samples comprising:

One-step extraction of HBV viral DNA from serum using phenol/chloroform;

PCR amplification of the coding region of HBV DNA polymerase (2400 base pairs) and its 3' non-coding region (310 base pairs). The 5' oligonucleotide includes a 5' proximal SP6 viral polymerase promoter;

In vitro translation of HBV DNA polymerase with PCR amplification products as template;

Activity assay on extracts containing the translated HBV DNA polymerase and in the presence of radiolabeled priming nucleotide.

Further subject matters of the present invention include reagents for implementing the method, a method of determining the inhibitory effect of substances on polymerase activity and an application on polymerase activity of HBV variants with mutations on the surface antigen.

In accordance with the present invention, serum sample may contain a HBV variant with unspecified DNA polymerase activity. The present invention enables its qualitative determination. For cases whereby quantitative measurements of the DNA polymerase activity are required, the activity assay in the present invention can be further developed (i.e. measurement of the primed DNA polymerase on nitrocellulose membranes). For cases whereby inhibitory effects of a molecule on the DNA polymerase are to be determined, the amount of primed DNA polymerase can be compared to that produced from a control sample where no inhibitory molecule is present.

For a better understanding of the present invention, reference will now be made, by way of example, to the following drawings:.

BRIEF DESCRIPTION OF THE DRAWINGS

FIG. 1 shows the linearized genomic structure of human HBV. The coding region of human HBV DNA polymerase (box) and its 3' non-coding region (the thicker line [in red]) included in the PCR amplification in the present invention. Numbers below represent position in the wild type human HBV genome of adw subtype, as defined in GenBank: Arrows indicate the positions and directions of the oligonucleotides used in the PCR amplification, and their sequences are displayed either above the arrow sign (5') or below (3'). In addition to the sequence matching the starting part of the HBV DNA polymerase (the first 27 bases of the coding region), the viral SP6 promoter (ATTTAGGTGA-CACTATAGAACTC, SEQ ID NO: 1) is incorporated in the 5' oligonucleotide. The location of the 5' sense oligonucleotide is from position 2309 to 2335 (arrow), whereas the 3' anti-sense oligonucleotide covers the region 1917 to 1940 (arrow).

GENERAL DESCRIPTION

Figure 1:
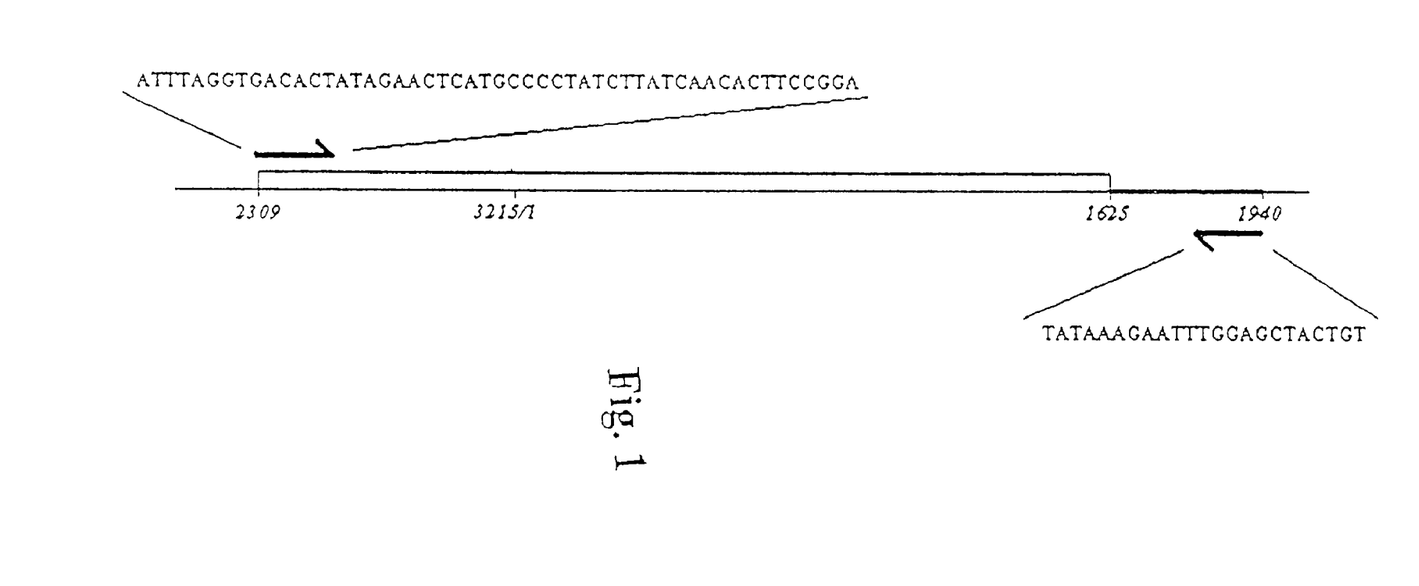
Figure 2:
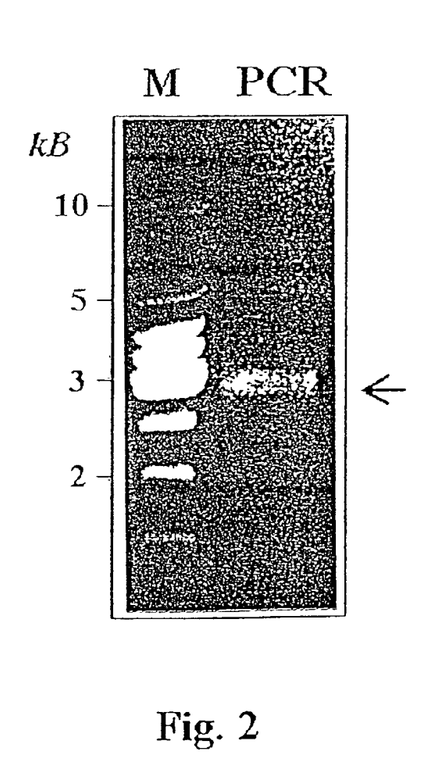
FIG. 2 is a photo which shows electrophoresis pattern of the PCR product amplified using viral DNA isolated from serum carrying wild type HBV. The fragment with the expected size of 2800 base pairs is indicated by an arrow. Also indicated on the 'M' lane are the migration positions of molecular size markers (1 kb DNA ladder, MBI Fermentas).

Wild type HBV viral DNA is extracted from serum sample by phenol/chloroform. PCR amplification is carried out in the first step of the present invention using specific oligonucleotides (FIG. 1). The 5' sense oligonucleotide matches the first 27 nucleotides of the coding region of HBV DNA polymerase and incorporates the SP6 promoter at its proximal end. The 3' antisense oligonucleotide has its matching region 300 base pairs downstream the stop codon of HBV DNA polymerase. The resulting linear DNA amplification products of 2800 base pairs (FIG. 2) are directly subjected to in vitro transcription/translation in the wheat germ cell-free system according to instructions provided by manufacturers (Promega, U.S.A.).

Figure 3:
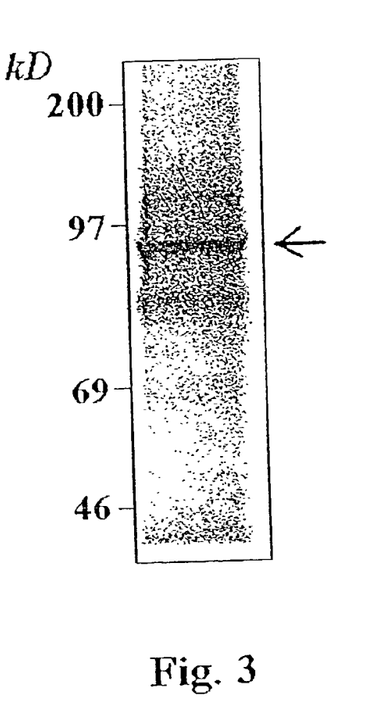
FIG. 3 is an autoradiograph which shows the in vitro translated wild type HBV DNA polymerase in wheat germ lysate, directly from the PCR amplification product in the presence of [$^{35}$S] methionine. The [$^{35}$S] labeled human HBV DNA polymerase of 90 kilo dalton (kD) as expected is indicated by an arrow. Indicated on the left outside are the positions of molecular size markers (Rainbow protein migration markers, Amersham).

When synthesized in the presence of [$^{35}$S] Methionine, in vitro translation yields a protein product with a molecular size of about 90 kD as expected for the 843 amino acid polymerase polypeptide shown on FIG. 3. This result is consistent with previous reports on DHBV DNA polymerase activity assay, and more importantly indicates that the human HBV DNA polymerase has been appropriately translated using the linear PCR amplification products as template.

To assay for the human HBV DNA polymerase activity, in vitro translation reaction mixture containing the newly synthesized polymerase in the absence of any radio-labeled amino acid (i.e. [$^{35}$S] Methionine) is incubated in a solution that contains dATP, dCTP, dGTP and radiolabeled [$\alpha$-$^{32}$P] dTTP. While any type of label that is conventionally used in the nucleotide assay arts may be used to label the nucleotides which will be incorporated into the primed polymerase, such as fluorescent or absorption labels, it is preferred to use a radiolabel. [$\alpha$-$^{32}$P] dTTP is chosen in the present invention because of its higher priming specificity as compared to the other three nucleotides.

Figure 4:
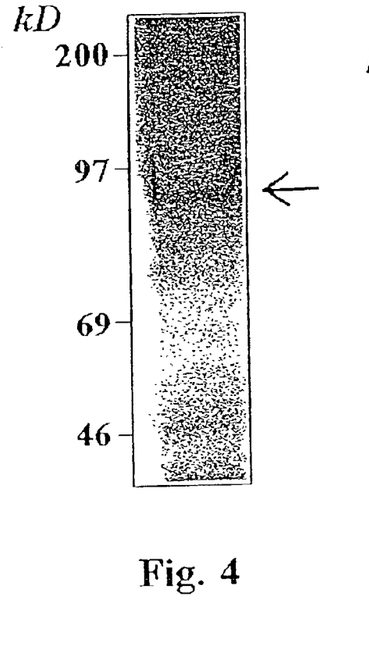
FIG. 4 is an autoradiograph that shows the in vitro priming activity of the wild type HBV DNA polymerase (synthesized in wheat germ lysate) in the presence of [$\alpha$-$^{32}$P] dTTP. The [$\alpha$-$^{32}$P] dTTP labeled human HBV DNA polymerase of 90 kilo dalton (kD) as expected is indicated by an arrow. Indicated on the left outside are the positions of molecular size markers (Rainbow protein migration markers, Amersham).
Figure 5:
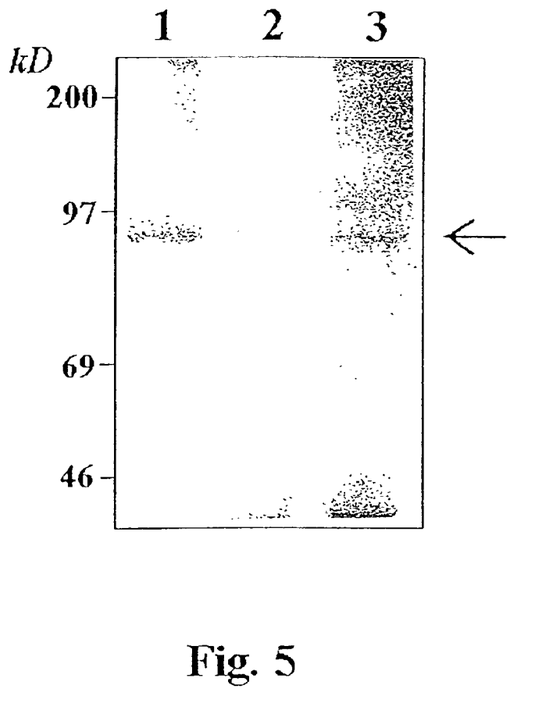
FIG. 5 is an autoradiograph that shows the in vitro priming activity of HBV DNA polymerases of the wild type (lane 1) and the surface antigen mutants 's' 145 (lane 2) and 's' 126 (lane 3) in the presence of [$\alpha$-$^{32}$P] dTTP. The [$\alpha$-$^{32}$P] dTTP labeled human HBV DNA polymerases of 90 kilo dalton (kD) as expected for all the three viral strains is indicated by an arrow. Indicated on the left side are the positions of molecular size markers (Rainbow protein migration markers, Amersham).

Depending on the type of label used, detection of the radiolabeled primed polymerase product may be achieved by any appropriate means. Generally this may include a step of separating labeled mononucleotides (i.e. [$\alpha$-$^{32}$P] dTTP) from radiolabeled primed polymerase product. In the present invention, the product of the priming reaction is preferably analyzed by SDS-polyacrylamide gel electrophoresis. FIG. 4 shows results of the priming activity assay on the human wild type HBV DNA polymerase in the presence of [$\alpha$-$^{32}$P] dTTP, the specific priming nucleotide for the human enzyme. The detection of the protein band of the expected size upon exposure to autoradiography indicates the priming activity of HBV DNA polymerase.

It will also be possible for the polymerase activity assay to be monitored by filtration through nitrocellulose membrane. Under appropriate conditions, quantitative binding of the radiolabeled primed polymerase can be observed with only an insignificant amount of unincorporated [α-$^{32}$P] dTTP being retained on nitrocellulose membrane.

The present invention is further illustrated by the following Examples; however, the present invention shall in no way be limited to these Examples.

EXAMPLES

General Experimental Methods

Viral DNA from serum carrying wild type HBV was isolated as follows. 200 μl of the serum sample was added to 400 μl of lysis buffer (Tris chloride 10 mM, pH7.4, EDTA 1 mM, and sodium dodecyl sulfate 2%) and 25 μl of proteinase K (20 mg/ml), incubated at 65° C. for 3 hours. Viral DNA was then extracted by phenol/chloroform and precipitated by ehanol. PCR amplification was carried out using the following oligonucleotides. The 5' oligonucleotide was a sense oligonucleotide (AAATTTAGGTGACACTAT AGAATATGCCCCTATCTTATCAACACTTCC, SEQ ID NO: 2) and contained a SP6 promoter at its proximal end (underlined sequence) and had its matching region at the starting region of the coding region of HBV DNA polymerase (position 2309 to 2340 in the wild type HBV genome). The 3' oligonucleotide was an anti-sense oligonucleotide (ACAGTAGCTCCAAATTCTT-TATAAGGGTCA, SEQ ID NO: 3) which has its matching region at 300 base pairs downstream of the stop codon of HV DNA polymerase (from position 1940 to 1911 in the wild type HBV genome). The resulting PCR product was therefore shorter than that established in published reports (by 50 base pairs). [α-$^{32}$P]dTTP (3000 Ci/mmole) and [$^{35}$S] methionine (1000 Ci/mmole) were obtained form Amersham. Unlabeled dATP, dCTP and dGTP were obtained from Promega.

Unless otherwise noted, the polymerase activity assay was conducted in solution containing 100 mM Tris HCl (pH 7.5), 10 mM MgCl$_2$, 30 mM NaCl, 10% glycerol, 4 mM dithiothreitol, 100 μM of each unlabeled deoxyribonucleotide triphosphates (dATP, dCTP and dGTP) and 5 μCi [α-$^{32}$P] dTTP. The reactions were incubated at 30° C. for 30 min, after which time a 5 μl aliquot was added to 85 μl of tricine sodium dodecyl sulfate-polyacrylamide gel electrophoresis (SDS-PAGE) sample buffer (Novex, U.S.A.), and 10 μl were analyzed on 10% SDS-PAGE. Following electrophoresis, gels were fixed by soaking in 10% methanol plus 10% acetic acid and dried under vacuum. Dried gels were exposed to X-ray film and signals quantified by laser densitometry.

Example 1

Polymerase Activity Assay on HBV Surface Antigen Mutants

One of the direct applications of the simplified activity assay on human HBV DNA polymerase reported in the present invention is to assess the relevant activity of variant HBVs with mutation on the major surface antigen, in particular those induced following vaccination (i.e. 's' 145). Viral DNA was extracted as described above from serum samples containing such HBV variants. The mutants involved in the present invention include 's' 145 (Glycine to Arginine mutation) and 's' 126 (Threonine to Alanine), which are capable of escaping the currently available immuno-based detection systems and capable of independent replication. Using the same pair of oligonucleotides, PCR amplification was carried out with the viral DNA as template on a DNA Thermal Cycler (Perkin-Elmer. Cetus) for 35 cycles using Taq polymerase (Promega, U.S.A.), each cycle consisting of 1.5 min at denaturing temperature (94° C., 2 min at annealing temperature (53° C.) and 4 min at extension temperature (72° C.).

The PCR product containing the SP6 promoter and amplified from each mutant HBV was added in wheat germ cell-free system. The coupled in vitro transcription/translation was carried out according to instructions provided by the manufacturer (Promega, U.S.A.). Briefly, 10 μl of PCR product was added to 25 μl of wheat germ extract supplemented with SP6 RNA polymerase, amino acid mixture (in the absence of [$^{35}$S] Methionine), RNAse inhibitor and reaction buffer. The reaction mixture was incubated at 30° C. for 60 min. The resulting extracts containing the translated HBV DNA polymerase were added to the solution described in General Experimental Methods, and the polymerase activity is assayed as above-mentioned. Results of such assay shown in FIG. 5 indicate that the HBV DNA polymerase of either the mutant 's' 145 (lane 2) or 's' 126 (lane 3) displays similar priming activity as compared with that of the wild type enzyme (lane 1). Alternatively, quantitative measurements may be carried out by laser densitometry that allows comparison of the intensity of the radiolabeled primed polymerases.

Example 2

Testing for Inhibitors of Human HBV DNA Polymerase

Screening for inhibitors of human HBV DNA polymerase would provide novel therapeutic agents for HBV infection, as effective inhibition of the polymerase activity will lead to inhibition of HBV viral replication. The simplified activity assay reported in the present invention would allow faster analysis of the inhibitory effects of newly found molecules on DNA polymerase of variant HBV carrying mutations on the major surface antigen. Briefly, a candidate inhibitor was first incubated with the wild type human HBV DNA polymerase that was PCR amplified and in vitro translated as reported in the present invention. The incubation was in the presence of [$\alpha$-$^{32}$P] dTTP and with other conditions identical as above-mentioned. Its inhibitory effect may be determined either by laser densitometry following SDS-PAGE analysis, or by measuring the amount of radiolabeled HBV DNA polymerase bound to nitrocellulose membrane after filtration. Significantly, the assay of inhibitory effects of such antiviral agents may be readily applied to HBV variants including the vaccine-induced mutant 's' 145 that is also involved in the present invention (FIG. 5). Further assay on the potential inhibitory effect derived from the above-mentioned assay may then be extended to other systems such as HBV-producing cell lines and transgenic animal model.

Depending on the type of label used, detection of the labeled hybrid HBV DNA polymerase product may be achieved by any appropriate means. Generally this may include a step of separating labeled mononucleotide from labeled human HBV DNA polymerase. In a preferred embodiment, detection is achieved by filtering the sample mixture (which at this point in the assay method, contains the labeled human HBV DNA polymerase and excess labeled mononucleotide) through a nitrocellulose membrane. The unincorporated excess labeled mononucleotide flows through the membrane while the labeled hybrid polymerase reaction product is captured on the nitrocellulose membrane. When the label is a radiolabel as is the case in the simplified assay reported in the present invention, then the amount of radioactivity bound to the filter may be quantified using a plate reading scintillation counter. Such measurement has distinct advantages over the prior one described in the present invention in that it does not involve an electrophoresis step.

Figure 6:
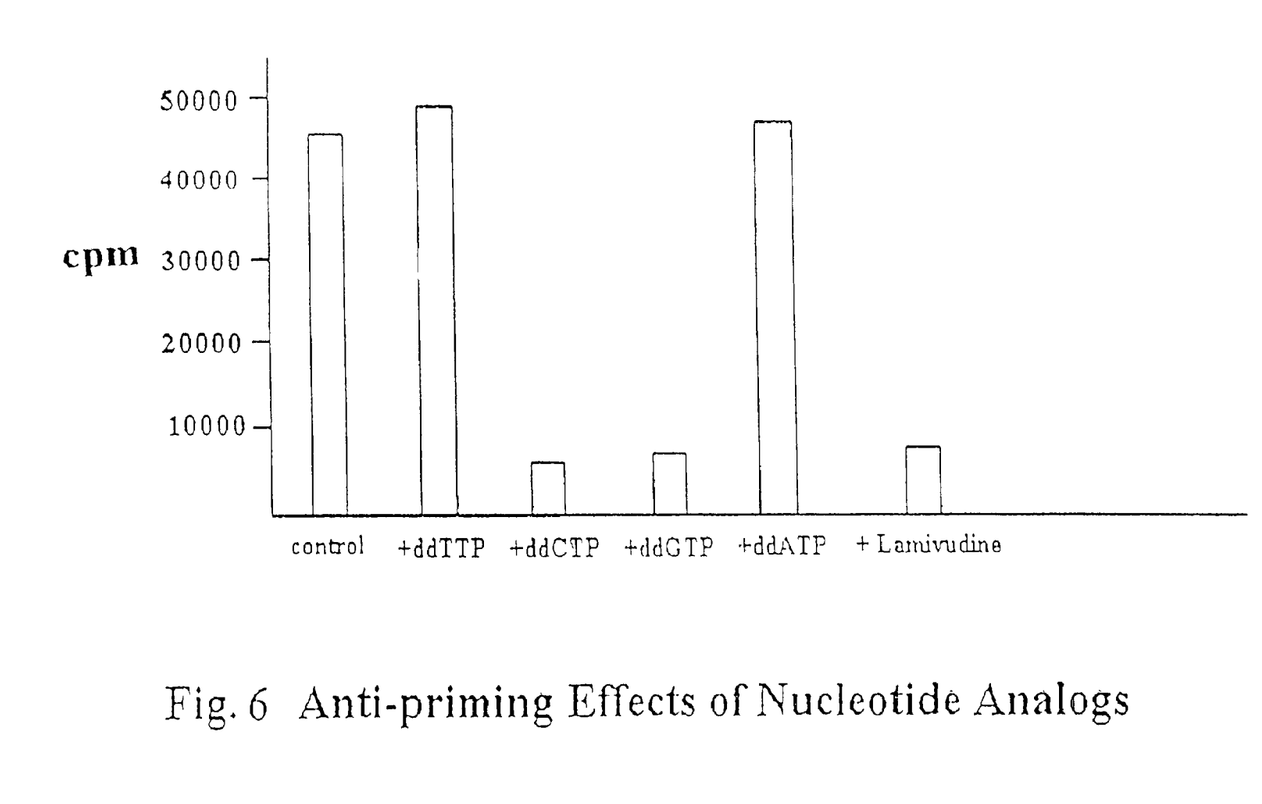
FIG. 6 is a summary of anti-priming effects of nucleotide analogs on the wild type human HBV DNA polymerase. Columns represent radiolabeled human HBV DNA polymerase remained on nitrocellulose membrane, as measured by cpm. Control indicates in vitro priming activity of human HBV polymerase in the absence of nucleotide analogs. Results of activity assays in the presence of particular nucleotide analog are indicated accordingly (i.e. +ddTTP for the activity assay in the presence of ddTTP). There is no obvious anti-priming effect when the incubation is carried out in the presence of either ddTTP or ddATP, as compared with the control. In contrast, inhibitory effect is observed with ddGTP, ddCTP. Consistent with our results, similar anti-priming effect is seen by addition of lamivudine which is a (−) enontiomer of 3'-thiacytidine, a cytosine dideoxynucleotide analog widely used clinically for treatment of HBV carriers with active HBV replication.

In the present invention, the following nucleotide analogs capable of inhibiting the HBV DNA polymerase activity may be assayed for their anti-priming activity. These include ddTTP, ddGTP, ddCTP, ddATP and lamivudine. Assay conditions are identical to those described in General Experimental Methods. Briefly, the nucleotide in the assay mixture is replaced with the corresponding nucleotide analog in the anti-priming testing of the particular nucleotide analog (i.e. dGTP should be replaced with ddGTP for testing the anti-priming activity of ddGTP). Conversely, no nucleotide is replaced when testing the anti-priming activity of ddTTP (as the radio-labeled nucleotide is dTTP in the present invention) as well as lamivudine. At the end of incubation, the reaction mixture is transferred onto a (2×2 cm) nitrocellulose membrane by gentle dotting. The unincorporated radio-labeled dTTP is then separated by washing the nitrocellulose membrane in 400 ml of Tris.HCl (pH. 7.5), 100 mM NaCl, 20 mM $MgCl_2$ and 0.5% bovine serum albumin. The remaining radiolabeled human HBV DNA polymerase bound to the nitrocellulose membrane is then measured quantified using a plate reading scintillation counter. Results shown in FIG. 6 indicate a significantly lower amount of [32P] labeled human HBV DNA polymerase in the presence of ddCTP and ddGTP as compared to the control assay (in the absence of any nucleotide analog), therefore pointing to their anti-priming activity. In contrast, no anti-priming activity is observed for either ddTTP or ddATP.

The present invention is based on a simplified activity assay on human HBV DNA polymerase. This invention makes possible fast determination of human HBV DNA polymerase activity directly from serum sample without the present requirement of cloning. Therefore it allows fast assessment and monitoring of the increasing number of variant HBVs with mutations on their major surface antigen. This invention also makes possible an easily accessible assay for inhibitory effects of antiviral agents on these HBV variants, with the particular emphasis on those that are induced following vaccination (i.e. 's' 145) related to liver diseases and those found in asymptomatic individuals which would eventually lead to liver disease.

The invention claimed is:

1. A method for producing HBV DNA polymerase, comprising:
   providing a 5' sense oligonucleotide comprising an SP6 promoter and an oligonucleotide sequence matching the 5' end of the human HBV DNA polymerase coding region;
   providing a 3' antisense oligonucleotide comprising an oligonucleotide sequence matching the 3' end of the human HBV DNA polymerase non-coding region;
   contacting the 5' oligonucleotide and 3' oligonucleotide with a sample containing a DNA encoding human HBV DNA polymerase;
   performing PCR amplification under conditions that allow amplification of the DNA encoding human HBV DNA polymerase to produce PCR products; and
   transcribing and translating the PCR products in eukaryotic cell-free lysates to produce in vitro translated human HBV DNA polymerase.

2. The method according to claim 1, wherein the 5' sense oligonucleotide encompasses the first 30 nucleotides of the coding region of human HBV DNA polymerase gene, the transcription promoter being located upstream of the HBV sequence in the 5 ' sense oligonucleotide.

3. The method according to claim 1, the 3' antisense oligonucleotide matches a region which is located 300 base pairs downstream of the stop codon of human HBV DNA polymerase gene.

4. The method according to claim 1, wherein the sample is a serum sample.

5. The method according to claim 4, wherein the serum sample contains either the human HBV wild type virus or a human HBV mutant virus.

6. The method according to claim 5, wherein the human HBV mutant virus is a surface antigen mutant.

7. The method according to claim 5, wherein the human HBV mutant virus is a mutant induced by HBV vaccine or a mutant from a patient with a hepatitis B liver disease.

8. The method according to claim 5, wherein the human HBV mutant virus is human HBV surface antigen mutant 's' 145 or 's' 126.

9. The method according to claim 1, wherein the eukaryotic cell-free lysates are wheat germ lysates.

10. The method according to claim 1, wherein transcribing and translating the PCR products in eukaryotic cell-free lysates includes transcribing and translating in the absence of any radio-labeled amino acid.

* * * * *

SEQUENCE LISTING

```
<160> NUMBER OF SEQ ID NOS: 3

<210> SEQ ID NO 1
<211> LENGTH: 23
<212> TYPE: DNA
<213> ORGANISM: Salmonella Typhimurium Phage SP6

<400> SEQUENCE: 1
atttaggtga cactatagaa ctc                                         23

<210> SEQ ID NO 2
<211> LENGTH: 48
<212> TYPE: DNA
<213> ORGANISM: Artificial sequence
<220> FEATURE:
<223> OTHER INFORMATION: Nucleotides 1-23 are SP6 promoter; nucleotides
      23-48 are from Hepatitis B Virus

<400> SEQUENCE: 2
aaatttaggt gacactatag aatatgcccc tatcttatca acacttcc              48

<210> SEQ ID NO 3
<211> LENGTH: 30
<212> TYPE: DNA
<213> ORGANISM: Hepatitis B virus

<400> SEQUENCE: 3
acagtagctc caaattcttt ataagggtca                                  30
```